(12) United States Patent
Lebert et al.

(10) Patent No.: US 6,856,395 B2
(45) Date of Patent: Feb. 15, 2005

(54) REFLECTOMETER ARRANGEMENT AND METHOD FOR DETERMINING THE REFLECTANCE OF SELECTED MEASUREMENT LOCATIONS OF MEASUREMENT OBJECTS REFLECTING IN A SPECTRALLY DEPENDENT MANNER

(75) Inventors: Rainer Lebert, Kelmis (BE); Ulf Heim, Ilmenau (DE); Lutz Aschke, Mainz (DE); Larissa Juschkin, Bochum (DE)

(73) Assignees: AIXUV GmbH, Aachen (DE); JENOPTIK Mikrotechnik GmbH, Jena (DE); Schott Glas, Mainz (DE)

( * ) Notice: Subject to any disclaimer, the term of this patent is extended or adjusted under 35 U.S.C. 154(b) by 483 days.

(21) Appl. No.: 10/120,863

(22) Filed: Apr. 11, 2002

(65) Prior Publication Data

US 2002/0175690 A1 Nov. 28, 2002

(30) Foreign Application Priority Data

Apr. 12, 2001 (DE) ......................................... 101 19 072

(51) Int. Cl.$^7$ .............................................. G01N 21/55
(52) U.S. Cl. ...................................................... 356/445
(58) Field of Search ................................ 356/445–448; 250/492.1, 492.2, 492.3, 306

(56) References Cited

U.S. PATENT DOCUMENTS

| | | | |
|---|---|---|---|
| 4,436,426 A | | 3/1984 | Smith |
| 5,747,813 A | * | 5/1998 | Norton et al. .............. 250/372 |
| 6,473,234 B2 | * | 10/2002 | Kuznetsov ................... 359/578 |
| 6,555,828 B1 | * | 4/2003 | Bokor et al. .............. 250/492.2 |
| 6,782,337 B2 | * | 8/2004 | Wack et al. ................. 702/155 |

OTHER PUBLICATIONS

Windt D.L. et al. "Multilayer Facilities Required for Extreme–Ultraviolet Lithography" Journal of Vacuum Science and Technology: Part B, American Institute of Physics, New York, USA, Bd. 12, No. 6 Nov. 1, 1994 pp. 3826–3932, XP 000497187.

Cui M. et al. "Synchrotron Radiation Soft X–ray Reflectometer and its Physics Results" Nuclear Instruments & Methods in Physics Research, Section–A: Accelerators, Spectrometers, Detectors and Associated Equipment, North–Holland Publishing Company, Amsterdam, NL, Bd. A359, No. 1. May 1, 1995, pp. 151–154, XP004009361.

Scriever G. et al. "Laser–Produced Lithium Plasma as a Narrow–Band Extended Ultravioletradiation Source for Photoelectron Spectroscopy" Applied Optics, Optical Society of America, Washington, USA Bd. 37, No. 7 1998 pp. 1243–1248, XP000920796.

* cited by examiner

Primary Examiner—Michael P. Stafira
(74) Attorney, Agent, or Firm—Reed Smith LLP

(57) ABSTRACT

In a reflectometer arrangement and a method for determining the reflectance of selected measurement locations on measurement objects reflecting in a spectrally dependent manner, the object of the invention is to reduce the time for measuring a measurement object with a robust and simple measurement structure to such an extent that compact radiation sources with low output compared to a synchrotron can be used at the site of production or of use of the measurement object to characterize the object characteristics in a manner suited to series production. A measurement beam bundle proceeding from a polychromatically emitting radiation source is directed onto the measurement location of the measurement object sequentially in modified manner by impressing spectral reference reflection characteristics and the radiation reflected from every measurement location is detected integrally. The arrangement and the method can be used with surfaces which reflect in a spectrally dependent manner and which are designed particularly for radiation in the extreme ultraviolet range.

11 Claims, 2 Drawing Sheets

REFLECTOMETER ARRANGEMENT AND METHOD FOR DETERMINING THE REFLECTANCE OF SELECTED MEASUREMENT LOCATIONS OF MEASUREMENT OBJECTS REFLECTING IN A SPECTRALLY DEPENDENT MANNER

CROSS-REFERENCE TO RELATED APPLICATION

This application claims priority of German application No. 101 19 072.7, filed Apr. 12, 2001, the complete disclosure of which is hereby incorporated by reference.

BACKGROUND OF THE INVENTION a) Field of the Invention

The invention is directed to a reflectometer arrangement for determining the reflectance of selected measurement locations on measurement objects reflecting in a spectrally dependent manner, with a polychromatically emitting radiation source whose radiation is directed onto the measurement object as a measurement beam bundle, and with a device for receiving reflected radiation from the selected measurement location. The invention is further directed to a method for determining the reflectance of selected measurement locations on measurement objects reflecting in a spectrally dependent manner which operates using a polychromatic measurement beam bundle directed to the measurement object.

b) Description of the Related Art

Preferable measurement objects are surfaces reflecting in a spectrally dependent manner for radiation in the extreme ultraviolet range (EUV) which achieve reflectivity in a narrow spectral range because of their layer construction. Up to one hundred layer pairs of different materials, e.g., alternating layers of silicon and molybdenum, with layer thicknesses in the range of a few nanometers and accuracies of <0.1 nm RMS are to be provided.

The production process for optics of the type mentioned above, particularly for use in EUV lithography, requires effective on-site quality controls which must be carried out at high throughput. A wavelength-dependent determination of the maximum reflectivity and a determination of the bandwidth of the spectral reflection curve within close tolerances are required. Typically, accuracies of better than 1% are demanded.

Since the quality assurance must guarantee that the product is constructed homogeneously with respect to its reflection characteristics, test measurements must be carried out to check the constancy of the measured values in as many locations as possible.

For example, when a mask with dimensions of approximately 150×150 mm$^2$ is to be measured with a spatial resolution of less than 0.2 mm$^2$, a measurement time of one hour requires a measurement frequency of more than 33 Hertz, that is, a measurement time of less than 30 milliseconds for each individual measurement point of the approximately 120,000 measurement points.

As is well known, a spectral reflection curve is always recorded in accordance with measurement techniques and, through its evaluation, the relevant parameters or characteristic values are obtained. Reflection curves of the kind mentioned above are contained in FIGS. 1 and 2. The curve in FIG. 1 corresponds to an "ideal" multilayer coating for EUV radiation of 13.5 nm at an incident angle of 5°. Deviations in the curve will occur when there are defects in the coating, which leads in FIG. 2 to a shifting of the "central wavelength" and the maximum reflectivity. The illustrated change corresponds to a defect in the layer thickness of 1% and interdiffusion of 1 nm.

Of all the usual methods for recording the reflection curve, in which either the wavelength varies at constant incident angle (λ-scan) or the incident angle varies at constant wavelength (θ-scan), the λ-scan delivers the most meaningful results because the characteristic values can be read out directly.

It is known to determine the spectral reflection of a sample, which is given by the ratio of reflected to radiated spectral photon flow $I_R$ and $I_O$, by means of reflectometers.

In the monochromatic concept, which can also be applied to synchrotrons, the radiation emitted by a polychromatic radiation source is directed in a monochromatic manner onto a measurement object and the reflected amplitude measured by means of an individual detector is compared with a separately emitted reference amplitude. (Windt, D. L. et al., "XUV Characterization Comparison of Mo/Si Multilayer Coating", X-Ray/EUV Optics for Astronomy, Microscopy, Polarimetry, and Projection Lithography, Eds. R. B. Hoover and A. B. C. Walker, Jr., Proceedings of SPIE 1343 (1991), p. 274, and Gullikson, E. M., et al., "A soft X-ray/EUV reflectometer based on a laser produced plasma source", Journal of X-Ray Science and Technology, October 1992, Vol. 3; (No. 4), 283–299).

The process to be repeated for all necessary wavelengths requires up to one hundred spectral measurement points per selected location on the measurement object and imposes high performance demands on the radiation source to achieve a sufficient photon flow per spectral measurement interval. Typical measurement times are in the range of one minute per location, for which reason this concept does not offer an effective quality control for series manufacture.

A polychromatic approach which is better suited to laboratory radiation sources provides for broadband irradiation of the measurement object and dispersion of the reflected radiation with a spectrograph prior to recording the different wavelengths by a line receiver or surface receiver (G. Schriever, et al., J. Appl. Optics, Vol. 37, No. 7, p. 1243 (1998). This is disadvantageous owing to the time required for the readout of the line receiver or surface receiver.

The recording of the spectral reflection curve which is always carried out in the art regardless of the concept applied disadvantageously increases expenditure on apparatus and impairs throughput by time-consuming measurements. The latter disadvantage occurs especially when the measurements are to be carried out on site, as is desirable. Since, in contrast to a synchrotron, the compact laboratory radiation sources or portable radiation sources required for this purpose have considerable disadvantages with respect to beam quality, particularly spectral brilliance, every attempt at complete characterization of a larger measurement object is hampered.

OBJECT AND SUMMARY OF THE INVENTION

Therefore, it is the primary object of the invention to reduce the time for measuring a measurement object with a robust and simple measurement structure to such an extent that compact radiation sources with low output compared to a synchrotron can be used at the site of production or use of the measurement object to characterize the object characteristics in a manner suited to series production.

According to the invention, this technical problem is solved by a reflectometer arrangement of the type mentioned above in that the radiation source for modifying the measurement beam bundle is followed in the beam path by a reflecting element with spectral reference reflection characteristics which directs the modified measurement beam bundle onto the measurement object, and in that the device for receiving the radiation reflected from the selected measurement location is constructed as an integral measuring detector.

For this purpose, in an advantageous manner, a part of the measurement beam bundle is applied to another detector whose generated signal, as reference signal, is proportional to the amount of radiation striking the measurement object. The detector is preferably arranged after the reflecting element.

Measurement objects can be EUV mask blanks, an EUV mask or multilayer mirrors.

Preferred radiation sources are pulsed laser radiation sources which can be based upon laser-generated or discharge-generated plasmas. A pinch plasma source, e.g., based on the HCT concept, is also particularly suitable.

Although the measurements are to be carried out with the arrangement according to the invention primarily with laboratory radiation sources, the use of a synchrotron is, of course, not excluded.

A further object of the invention is a method for determining the reflectance of selected measurement locations on measurement objects reflecting in a spectrally dependent manner using a polychromatic measurement beam bundle which is directed to the measurement object, wherein the measurement beam bundle is directed onto the measurement location of the measurement object sequentially in modified manner by impressing spectral reference reflection characteristics and the radiation reflected from every measurement location is detected integrally.

Due to the fact that the measurement beam bundle is prepared by impressing a reference reflection curve, the signal of the reflected radiation which is measured integrally and serves as a measure of the conformity between the reference characteristics and actual characteristics is extremely sensitive to differences in the reflection characteristics of the individual measurement points.

Instead of time-consuming measurement of the exact spectral reflection curve and complicated evaluation thereof, a simple detector (e.g., a photodiode) is sufficient for signal recording, so that the entire system is simple, compact in construction and fast. Further, the concept uses all of the photons emitted by the radiation source in the measurement bandwidth for measurement, resulting in extremely short measurement times and increased sensitivity by a factor of 100 compared to the polychromatic approach and by a factor of 10,000 compared to the monochromatic concept. Accordingly, it is possible to measure an individual spatial measurement point with an individual pulse of a typical EUV laboratory radiation source.

The invention will be described more fully in the following with reference to the schematic drawings.

DESCRIPTION OF THE PREFERRED EMBODIMENTS

Figure 3:
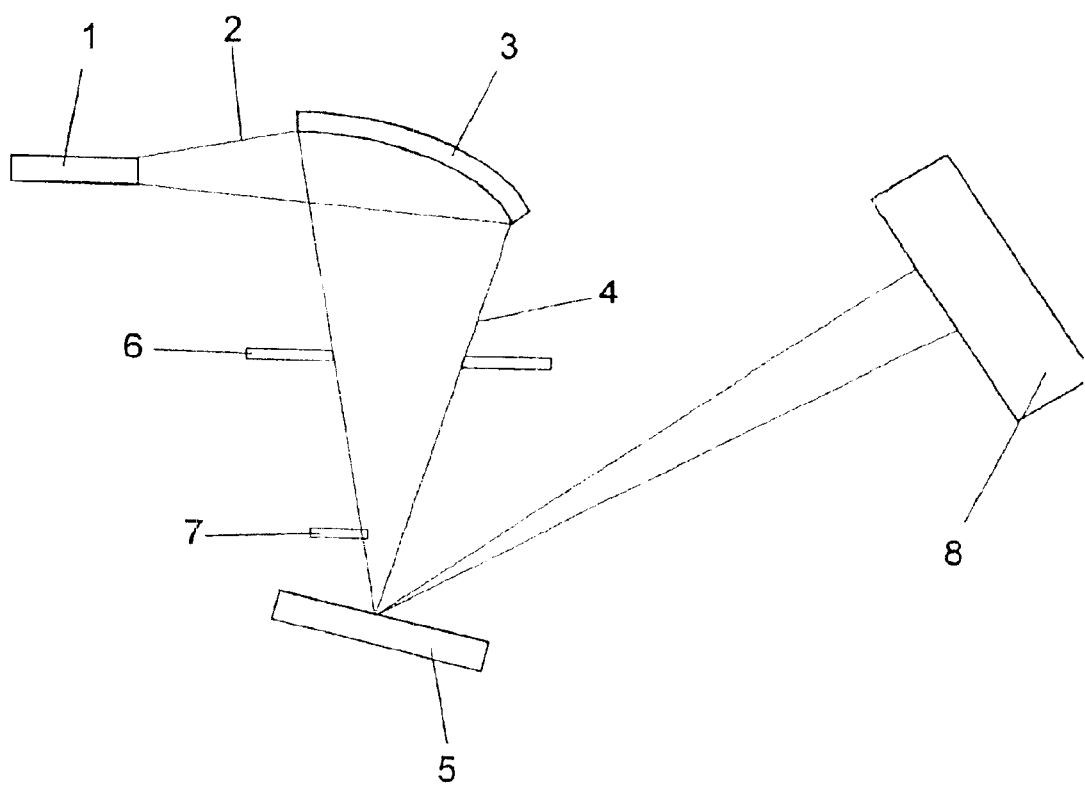
FIG. 3 shows a reflectometer arrangement according to the invention for measuring highly reflecting surfaces.

According to FIG. 3, radiation from a radiation source 1 (EUV radiation source), which emits polychromatically in the extreme ultraviolet range and which, as pulsed laboratory radiation source, can be based, e.g., on a laser-generated plasma (LLP) or discharge-generated plasma, is directed as a measurement beam bundle 2 to a reflection element which is arranged downstream in the beam path in the form of a multilayer mirror 3 with spectral reference reflection characteristics. The latter modifies the measurement beam bundle 2 to form a measurement beam bundle 4 and can either be constructed as a plane mirror or, as a curved mirror, can increase the radiation flow onto a measurement object 5 or can be used for advantageously changing the geometry of the modified measurement beam bundle 4.

While the use of laboratory radiation sources is preferred, it is also possible, if necessary, to use the radiation of a synchrotron as measurement beam bundle 2.

A diaphragm 6 arranged between the multilayer mirror 3 and the measurement object 5 ensures that only an area on the measurement object 5 that is selected for measurement is irradiated by the modified measurement beam bundle 4 as measurement location. Of course, it is also possible to use the focus of the multilayer mirror 3 which is curved in a suitable manner or other EUV optical elements for this purpose.

Since the pulses emitted by the radiation source 1 can fluctuate in intensity (by approximately 2% to 5%), a beam monitor 7, as it is called, is provided and serves to determine the amount of radiation impinging on the measurement object 5. This is an EUV-sensitive detector, e.g., a photodiode, which is irradiated by a portion of the modified measurement beam bundle 4 which is advantageously removed after reflection at the multilayer mirror 3 and whose generated signal, as reference signal, is proportional to the amount of radiation striking the measurement object 5. It is also possible to use other measurement principles such as detection of photoelectrons.

In order to derive a measurement signal in the form of an individual intensity signal, the amount of radiation reflected by the measurement object 5 is directed to a detector 8 which, as an EUV-sensitive photodiode or EUV-sensitive CCD camera, is arranged subsequent to the measurement object 5 in the beam path and which also allows further information to be obtained about the measurement object 5 (e.g., scattered light).

Due to the pulsed operation of the radiation source 1, the measurement object 5 to be examined can be moved continuously for selecting the measurement location at a speed of $$V = \Delta x \cdot R_Q$$

($\Delta x$=required spatial resolution, $R_Q$=repetition rate of the radiation source [Hz]).

If the polychromatic radiation proceeding from the radiation source were directed onto the measurement object 5 directly, a voltage signal would be obtained at the detector 8 with each emission pulse of the radiation source 1, given by the following equation from the spectral distribution of the radiated output ($\Theta(\lambda)$), the spectral reflection curve (R(λ)) and the sensitivity of the photodiode being used ($C_{Diode}$):

$$S_{Mess} = c_{Diode} \cdot \int_0^\infty \Theta_Q(\lambda) \cdot R(\lambda) \, d\lambda.$$

While the reference signal measured by the beam monitor 7 is proportion to the integral $$S_{Ref} = c_{Ref} \cdot \int_0^\infty \Theta_Q(\lambda) \, d\lambda$$

of the incident radiation output of the radiation source 1, the quotient of the two measured quantities is proportional to the integral over the spectral reflection curve weighted by the emission characteristic of the radiation source 1.

In order to obtained reliable information about the parameters of the reflection of the measurement object 5, the measurement results are weighted by a filtering of the measurement beam bundle 2 in that the information about the sought for reflection curve is already impressed on the latter.

This is achieved in the invention by means of the multilayer mirror 3 which reflects with a respective reference value in the central wavelength at maximum reflectivity and bandwidth and accordingly has a spectral reference reflection curve $R_{Ref}(\lambda)$. Owing to the modification of the measurement signal $S_{Mess}$ and reference signal $S_{Ref}$ by the reference reflection curve $R_{Ref}(\lambda)$ $$S_{Mess} = c_{Diode} \cdot \int_0^\infty \Theta_Q(\lambda) \cdot R(\lambda) \cdot R_{Ref}(\lambda) \cdot d\lambda.$$

and $$S_{Ref} = c_{Ref} \cdot \int_0^\infty \Theta_Q(\lambda) \cdot R_{Ref}(\lambda) \cdot d\lambda,$$

the ratio of the scalar quantities of the two intensity signals $S_{Mess}$ and $S_{Ref}$ is very highly sensitive to every defect in the examined measurement object 5 irrespective of the behavior of the radiation source 1. In contrast to the monochromatic concept in which the spectral reflection curve comprising a large number of scalar measurement values for each measurement location must undergo a cumbersome evaluating process, the quality-determining information is practically immediately available in the invention for every measurement location with the integrally determined measurement value, and the quality increases as the measurement value increases. The absolute value size can be calibrated at a sample in addition or can be calculated for the specific construction.

However, assuming that the measurement objects 5 to be examined have a high quality standard considered by themselves, calibration can be omitted. This applies particularly when the goal is to verify the homogeneity of the reflection characteristics of a reflecting surface, e.g., of a mask blank, and when it is sufficient to search for measurement locations with sharp deviations.

The invention is particularly well suited to this purpose because the measurement signal reacts sharply to a variation in the central wavelength, where a measurement accuracy of 2% is sufficient for detecting a deviation of 0.2% in the central wavelength; a deviation of 0.5% in the central wavelength already changes the measurement signal by 11.8%. When the bandwidth varies by a value of x%, the measurement signal changes by x/2%. With fluctuations in maximum reflectivity, the measurement signal reacts linearly, i.e., with a variation of x% in the measurement signal to a fluctuation of x%.

Figure 1:
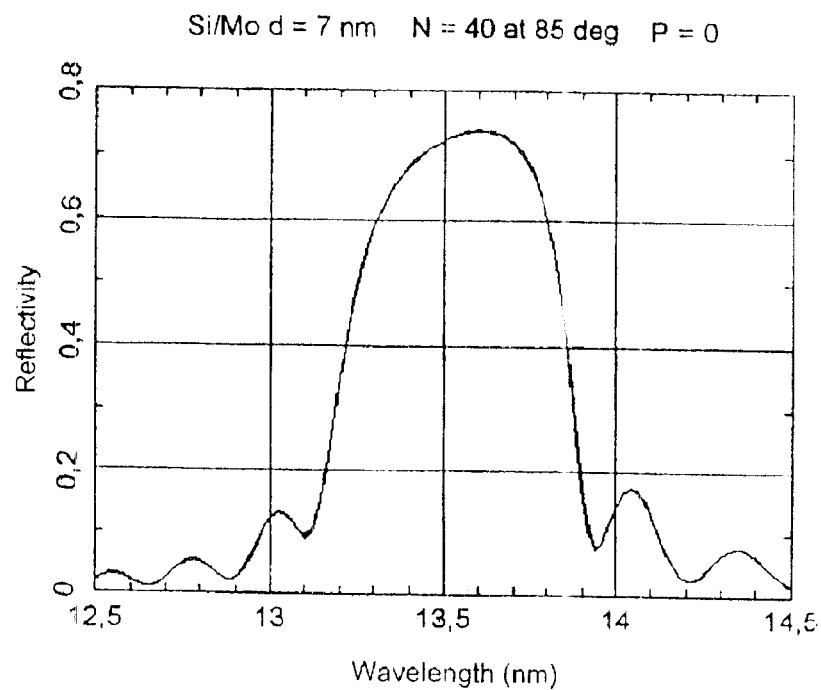
FIG. 1 shows a spectral reflection curve of an "ideal" multilayer coating for an EUV radiation of 13.5 nm and incident angle of 5°.
Figure 2:
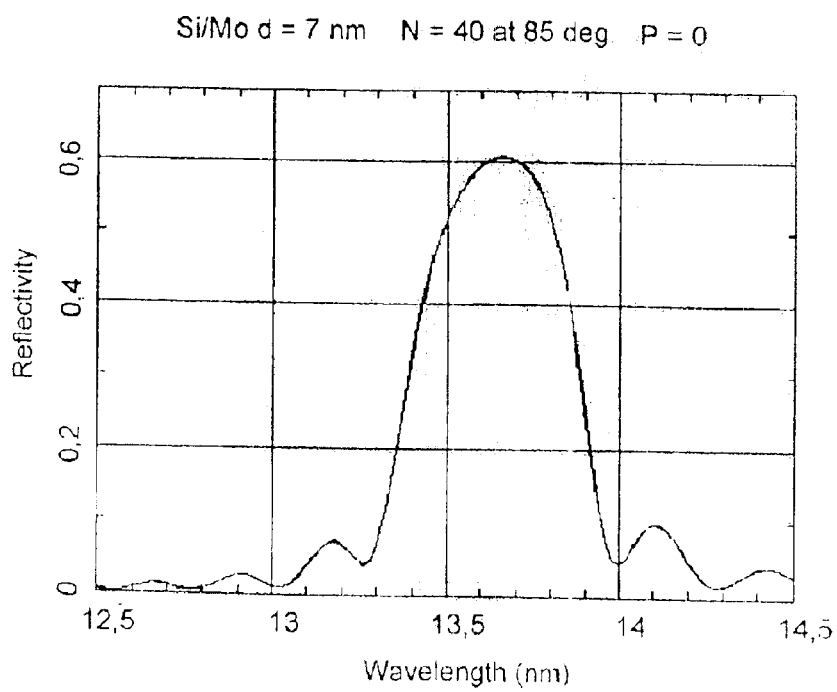
FIG. 2 shows a spectral reflection curve of a multilayer coating for EUV radiation with a layer thickness error of 1% and interdiffusion of 1 nm.

The reflection curves shown in FIGS. 1 and 2 give a signal reduction of 33.4% in a measurement according to the invention. In order to minimize noise in the measurement signal, at least $10^8$ photons must be measured in the measurement interval, which, with an average reflectivity of 25%, requires approximately $4 \times 10^8$ photons radiated from the radiation source 1 to the measurement object 5, corresponding to an output of approximately 200 nW of the radiation source 1 constructed as an EUV source. With typical outputs of available EUV sources of 25 mW/sr/2% bandwidth, a solid angle of $10^{-5}$ sr, that is, an aperture angle of <0.2 degrees, is sufficient.

While the foregoing description and drawings represent the present invention, it will be obvious to those skilled in the art that various changes may be made therein without departing from the true spirit and scope of the present invention.

What is claimed is:

1. A reflectometer arrangement for determining the reflectance of selected measurement locations on measurement objects reflecting in a spectrally dependent manner, comprising:
   a polychromatically emitting radiation source whose radiation is directed onto the measurement object as a measurement beam bundle;
   a device for receiving reflected radiation from the selected measurement location;
   said radiation source for modifying the measurement beam bundle is followed in the beam path by a reflecting element with spectral reference reflection characteristics which directs the modified measurement beam bundle onto the measurement object; and
   said device for receiving the radiation reflected from the selected measurement location is constructed as an integral measuring detector.

2. The reflectometer arrangement according to claim 1, wherein a part of the measurement beam bundle is applied to another detector whose generated signal, as reference signal, is proportional to the amount of radiation striking the measurement object.

3. The reflectometer arrangement according to claim 2, wherein the detector is arranged after the reflecting element.

4. The reflectometer arrangement according to claim 1, wherein the measurement object is an EUV mask blank or an EUV mask.

5. The reflectometer arrangement according to claim 1, wherein the measurement object is a multilayer mirror.

6. The reflectometer arrangement according to claim 4, wherein the radiation source is a pulsed laser radiation source.

7. The reflectometer arrangement according to claim 6, wherein the radiation source is based upon a laser-generated plasma.

8. The reflectometer arrangement according to claim 6, wherein the radiation source is based upon a discharge-generated plasma.

9. The reflectometer arrangement according to claim 6, wherein the radiation source is a pinch plasma source, based on the HCT concept.

10. The reflectometer arrangement according to claim 4, wherein the radiation source is a synchrotron.

11. A method for determining the reflectance of selected measurement locations on measurement objects reflecting in a spectrally dependent manner comprising the steps of:
   directing a polychromatic measurement beam bundle to the measurement object;

said measurement beam bundle being directed onto the measurement location of the measurement object sequentially in modified manner by impressing spectral reference reflection characteristics; and detecting the radiation reflected from every measurement location integrally.

* * * * *